(12) United States Patent
McVey et al.

(10) Patent No.: US 7,592,500 B2
(45) Date of Patent: Sep. 22, 2009

(54) ACTIVATED OXIDIZING VAPOR TREATMENT METHOD

(75) Inventors: Iain F. McVey, Lakewood, OH (US); Lewis I. Schwartz, Shaker Heights, OH (US); Michael A. Centanni, Parma, OH (US); Gerald E. McDonnell, Basingstoke (GB)

(73) Assignee: Steris Inc., Temecula, CA (US)

( * ) Notice: Subject to any disclaimer, the term of this patent is extended or adjusted under 35 U.S.C. 154(b) by 998 days.

(21) Appl. No.: 10/422,474

(22) Filed: Apr. 24, 2003

(65) Prior Publication Data

US 2004/0057868 A1 Mar. 25, 2004

Related U.S. Application Data

(60) Provisional application No. 60/375,851, filed on Apr. 24, 2002.

(51) Int. Cl.
*A62D 3/38* (2007.01)

(52) U.S. Cl. ...................................... 588/320; 588/401

(58) Field of Classification Search ................ 588/313, 588/318, 320, 401, 405, 309, 321; 422/26, 422/37
See application file for complete search history.

(56) References Cited

U.S. PATENT DOCUMENTS

| | | | |
|---|---|---|---|
| 4,695,327 A | 9/1987 | Grebinski | 134/11 |
| 4,896,547 A | 1/1990 | Arney et al. | 73/863.81 |
| 5,430,228 A | 7/1995 | Ciambrone et al. | 588/200 |
| 5,714,128 A | 2/1998 | Ritter | 422/211 |
| 6,011,193 A * | 1/2000 | Myler et al. | 588/318 |
| 6,080,906 A * | 6/2000 | Johnson et al. | 435/262.5 |
| 6,096,283 A * | 8/2000 | Cooper et al. | 423/437.1 |
| 6,121,506 A * | 9/2000 | Abel et al. | 588/318 |
| 6,245,957 B1 | 6/2001 | Wagner et al. | 588/200 |
| 6,375,697 B2 | 4/2002 | Davies | 55/340 |
| 6,790,249 B2 | 9/2004 | Davies | 55/340 |
| 2001/0049926 A1 | 12/2001 | Davies | 55/385.2 |
| 2003/0035754 A1 | 2/2003 | Sias et al. | 422/29 |

FOREIGN PATENT DOCUMENTS

| | | |
|---|---|---|
| DE | 19732594 | 2/1999 |
| EP | 1 166 825 A1 | 1/2002 |
| FR | 2651133 | 3/1991 |
| JP | 2002066308 | 3/2002 |

* cited by examiner

*Primary Examiner*—Edward M Johnson
(74) *Attorney, Agent, or Firm*—Fay Sharpe LLP

(57) ABSTRACT

An oxidizing liquid (20), such as hydrogen peroxide, is vaporized (18) and the vapor is used to deactivate nerve gas, blistering gas, or other biologically active substances such as pathogens, biotoxins, and prions. A second chemical compound (42) in vapor, mist, or fog form is used in conjunction with the oxidizing vapor. In one embodiment, the second chemical preconditions the biologically active substances to be deactivated more efficiently by the oxidizing vapor. In another embodiment, the second chemical boosts the reactivity of the oxidizing vapor. In another embodiment, the other chemical reacts with the oxidizing vapor to form an intermediate compound that deactivates at least some of the biologically active substances.

29 Claims, 2 Drawing Sheets

US 7,592,500 B2

ACTIVATED OXIDIZING VAPOR TREATMENT METHOD

This application claims priority to U.S. Provisional Application Ser. No. 60/375,851, filed Apr. 24, 2002.

BACKGROUND OF THE INVENTION

The present invention relates to the art of treating articles with highly reactive oxidant vapors. It finds particular application in conjunction with deactivating biological and chemical warfare agents, such as blistering agents (e.g., mustard gas), acetyl cholinesterase inhibitors (e.g., nerve gas), and biotoxins (e.g., botulinum toxin) and will be described with particular reference thereto. However, it is to be appreciated, that the present invention will find application in conjunction with the oxidation of other substances.

Liquid oxidants have been developed which can deactivate biological warfare agents. See, for example, U.S. Pat. No. 6,245,957 to Wagner, et al. In Wagner, a strong oxidant solution is sprayed as a liquid or foam onto equipment in the field which is or has potentially been contaminated with biological and chemical warfare agents. After treatment, the solution is rinsed from the equipment with water, which can be permitted to flow onto the ground, as it is nontoxic. Although effective, the liquid Wagner solution has drawbacks. First, it is difficult for liquids to penetrate crevices, fine cracks, ducts, and partially protected or lapping parts. Second, in enclosed spaces, such as in the interior of airplanes and buildings, cleanup and disposal of the liquid solution can be problematic. Third, liquids can damage some equipment, such as electronic or electrical equipment.

The present application delivers the strong oxidant to the surfaces to be decontaminated in a vapor phase to facilitate penetration and cleanup.

SUMMARY OF THE INVENTION

In accordance with one aspect of the present invention, biological and chemical warfare agent residues are deactivated by oxidation with a vapor phase oxidant.

In accordance with another aspect of the present invention, a means is provided for oxidizing biological and chemical warfare agents with an oxidant vapor.

One advantage of the present invention resides in its improved penetration.

Another advantage of the present invention resides in its ease of cleanup.

Another advantage resides in compatibility with electrical equipment.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
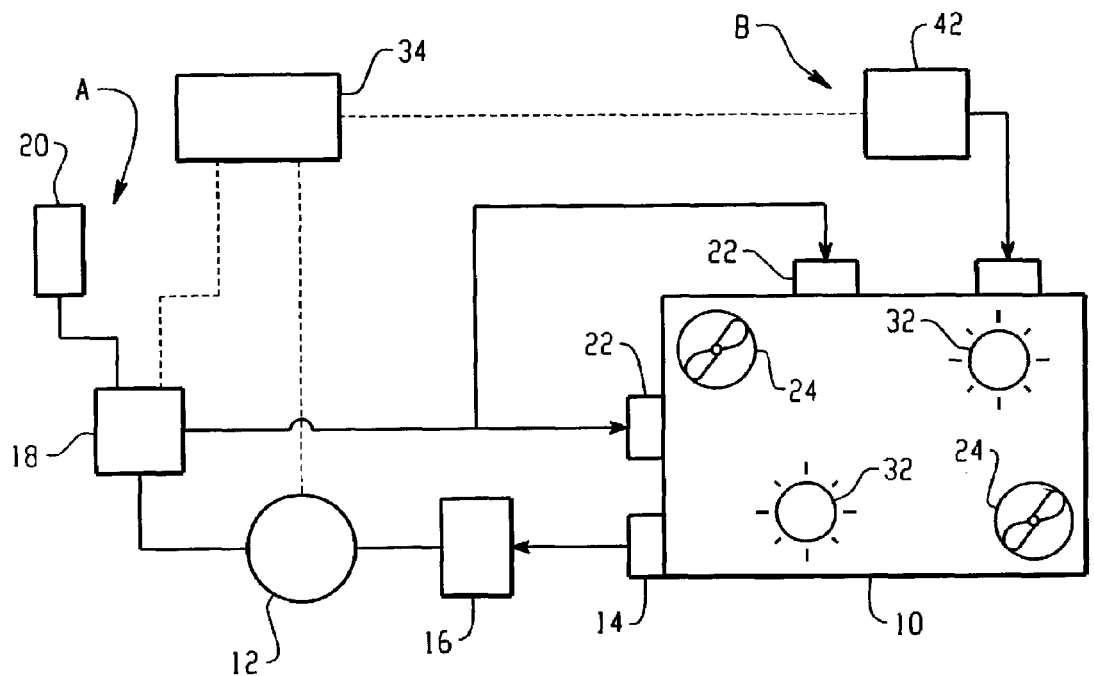
FIG. 1 is a diagrammatic illustration of a vapor strong oxidant treatment system in accordance with the present invention.

With reference to FIG. 1, a treatment enclosure 10 receives or is itself part of the structure potentially contaminated with biologically active substances such as biological or chemical warfare agents to be treated with vapor oxidant compounds. Typical biologically active substances include pathogens, biotoxins, prions, chemical agents such as nerve gas or blistering agents, and the like. The treatment enclosure, in one embodiment, is a chamber that is adapted to receive items to be treated and then sealed. In another embodiment, the enclosure includes the interior of a warehouse, room, aircraft or other vehicle, tent, or the like which is or whose surfaces or items contained in the enclosure are to be treated.

A warfare agent oxidizing means A includes a pump 12 that draws the environmental gas, typically air, from the enclosure through an optional biological and chemical hazard filter 14 or other means for preventing contamination in the enclosure from escaping and preferably through a dryer 16. In a preferred hydrogen peroxide vapor embodiment, the dryer also includes a catalyst that breaks down the hydrogen peroxide vapor to water for removal by the dryer. The blower blows the filtered and dried air into a vaporizer 18, which vaporizes a liquid oxidant compound from a liquid oxidant supply 20. The vapor is blown through another optional biological contaminant filter 22 or other means for preventing contamination in the enclosure from escaping into the chamber 10. Optionally, the output of the vaporizer is branched or fed to a manifold that feeds the oxidant vapor into the enclosure from a plurality of locations. Optionally, additional fans or blowers 24 are placed in the enclosure to circulate the vapor and improve uniformity of concentration and distribution of the vapor. The preferred oxidant liquid includes peroxy compounds such as hydrogen peroxide and peracetic acid. The use of other oxidants such as hypochlorites, solutions of ozone, and the like are also contemplated. Optionally, the oxidant compound is mixed with an alcohol to generate an alcohol vapor which functions as a cosolvent. When the materials in the contaminated structure permit, the temperature of the structure is preferably raised to 70° C. which allows extraction of the agent from the material and facilitates reaction with the oxidant vapor. Moreover, higher temperatures permit higher concentrations of oxidant vapor without condensation problems. Of course, when plastics or temperature sensitive electronics are involved, temperatures of 45°-60° C. may be preferred.

In the embodiment of FIG. 1, a chemical delivery means system B delivers other chemistry in a vapor, mist, or fog form directly into the enclosure 10. The delivery means B includes a source 42 of other chemical vapor, mist, or fog. In one embodiment, the other chemistry delivery system includes filters, blowers, and vaporizers, analogous to those described for the oxidant vapor. In another embodiment, a liquid chemical is sprayed with a misting nozzle or fogged with a fogger directly into the enclosure. In yet another embodiment, a reservoir or cylinder of the other chemical in gaseous form is provided.

The other chemistry in one embodiment is selected (1) to activate the oxidant vapor to a higher oxidation potential, (2) to increase the number and diversity of reactive species, (3) to precondition the target substances to make them more susceptible to attack by the oxidant vapor, or (4) to react with the oxidant vapor to form an intermediate compound that attacks all or some of the target substances. In one preferred embodiment, the oxidant vapor is hydrogen peroxide in a concentration of 25-75%, with about 50% preferred. In one embodiment, the other chemistry includes short alkene chains and water vapor, which interacts with the peroxide vapor to form a number of radical species, such as singlet pairs of oxygen, methyl radicals ($CH_3^-$), hydroxyl radicals ($OH^-$), hydroperoxy radicals ($OOH^-$), and others. Alternately, the other delivery system delivers ozone, aldehydes, peroxy carboxylic acid, or the like to the chamber in vapor, mist, or fog. Optionally, UV light sources are used, in addition to or instead of, the chemical delivery system to enhance the reactive species.

In another embodiment, the other chemistry includes a condensable solvent vapor, mist, or fog that is miscible with water and produces a solution with reduced polar properties is condensed on the target substance. Suitable solvents include tertiary butyl alcohol (tBuOH), formic acid, peracetic acid, other alcohols, acetone, or acetyl nitrite.

In another embodiment, the other chemistry adjusts pH. To lower pH, acetic or formic acid is preferred. Ammonia is preferred for raising the pH. Typically, strong oxidants have a low pH which is advantageously raised to near neutral.

Although only a single other chemistry delivery system is illustrated in FIG. 1, it is to be appreciated that individual delivery systems can be provided for the various above-discussed other chemistries.

A control 34 controls the other chemistry delivery system or means B and the peroxy vapor delivery system or means A. In one embodiment, the peroxy vapor and other chemistry are delivered concurrently into the enclosure. In another embodiment, the other chemistry is added to the enclosure first to precondition the biologically active substances. For example, injecting a cosolvent vapor and allowing it to condense prior to the hydrogen peroxide for partially dissolving or otherwise making biologically active substances that are not soluble in the oxidant vapor more readily penetrated by the oxidant vapor are contemplated. In another embodiment, the oxidant vapor is added to the enclosure first to establish equilibrium and start deactivating the biologically active substances that are more readily oxidized. Then the other chemistry is added to boost the reactivity of the oxidant vapor or to generate an intermediate vapor compound to attack the remaining biologically active substances.

Figure 2:
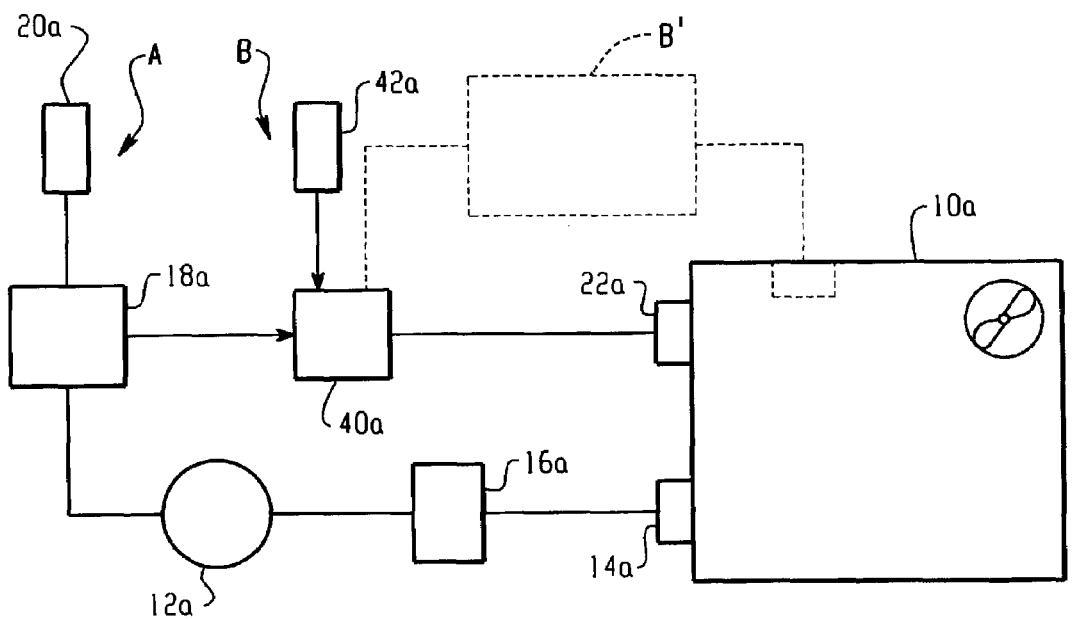
FIG. 2 is an alternate embodiment of the oxidant vapor treatment system.

With reference to FIG. 2, a blower 12a draws atmospheric air from an enclosure 10a through a biologically active substance exit inhibiting means 14a such as a filter or valve and a dryer 16a. The blower blows the atmospheric gases through a vaporizer 18a that vaporizes a peroxy liquid, preferably hydrogen peroxide from a source 20a. The peroxy vapor is passed to a mixing chamber 40a where the other chemistry delivery means B mixes the peroxy vapor with the other chemistry from a source 42. In one embodiment, the mixing chamber 40 adds water vapor and short chain alkene vapor, aldehyde vapor, peroxycarboxylic acid vapor, or the like, to the peroxy vapor to form singlet oxygen, hydroperoxy, and other reactive radicals. In other embodiments, solvents or pH adjusting compounds are mixed with the oxidant vapor in the mixing chamber 40a. Alternately, the other chemistry reacts with the peroxy vapor to form an intermediate compound as described above. The modified vapor is passed through a biologically active substance escape inhibiting means 22a, such as a filter or check valve, into the enclosure 10a. The means 14a and 22a prevent contamination in the enclosure from migrating into the lines of the vapor delivery system. Optionally, another chemistry delivery system B' delivers a preconditioning vapor, mist, or fog, ammonia gas, or solvent vapor, as described above, directly into the enclosure or into the mixing chamber 40a.

Figure 3:
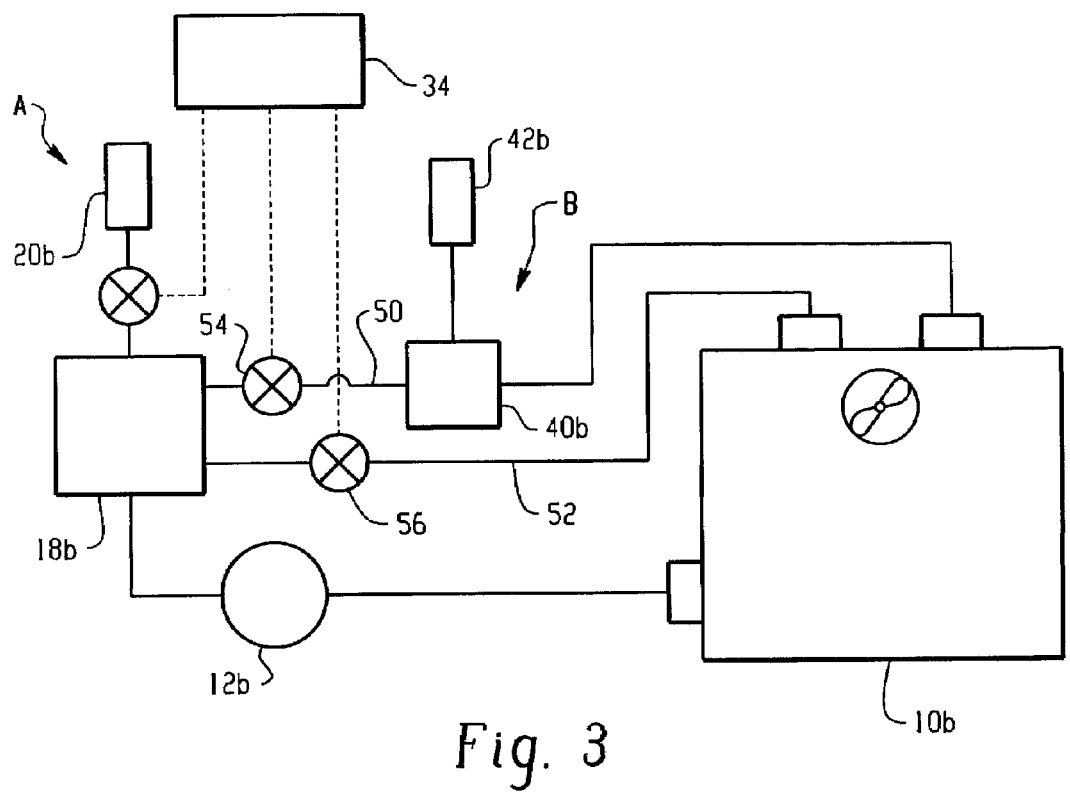
FIG. 3 is another alternate embodiment of the oxidant vapor treatment system; and, FIG. 4 is yet another alternate embodiment of an oxidant vapor treatment system.

With reference to the embodiment of FIG. 3, a blower 12b blows the atmospheric air from an enclosure 10b through a vaporizer 18b of the oxidant vapor means A. The output of the vaporizer is split between one path 50, which delivers the vapor directly to the enclosure 10b, and a second path 52 that delivers the vapor through a mixing chamber 40b of the other chemical delivery means B to the enclosure 10b. Valves 54, 56 in lines 50 and 52 are controlled by a control system 34b for dynamically adjusting the proportion of the oxidant vapor that passes through the mixing chamber to control the amount of gaseous other chemistry introduced into the chamber.

Figure 4:
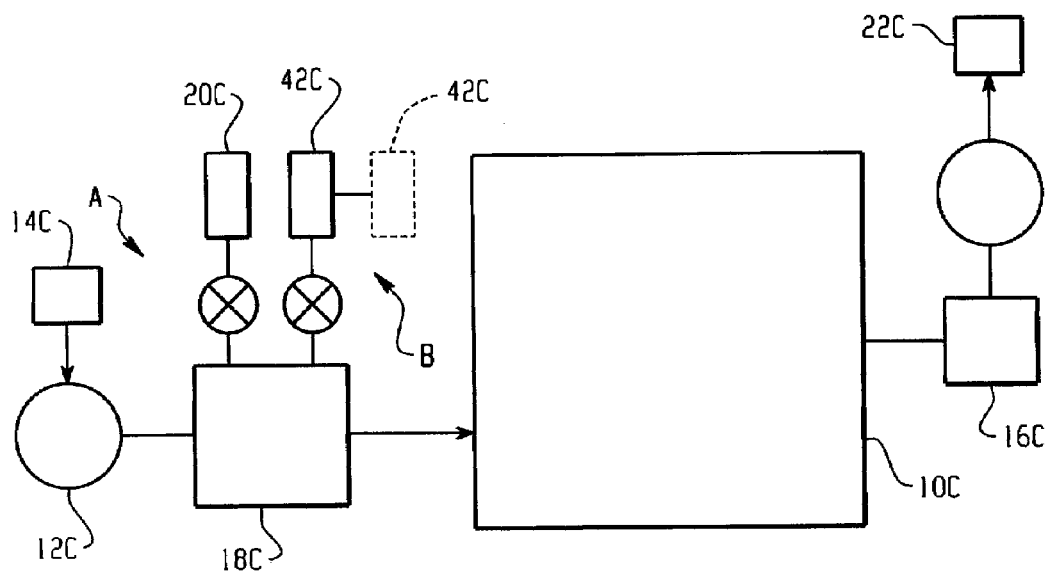

With reference to FIG. 4, a blower 12c pulls atmospheric air through a filter 14c and blows it into a vaporizer 18c. The vaporizer 18c is connected with an oxidant liquid source 20c and at least one additional source of other chemistry 42c. The oxidant liquid and the other chemistry(ies) are vaporized concurrently or sequentially in the vaporizer and fed to a treatment enclosure 10c. Alternately, one or more other chemicals are supplied in gaseous form and mix in the vaporizer with the oxidant and other chemical vapors. Air from the treatment enclosure can be recirculated as described in the first three embodiments. However, in the illustrated embodiment, the air and vapor pass from the chamber to an oxidant and other chemistry deactivator 16c such as a catalyst, and are blown through a biological filter 22c into the atmosphere. Optionally, the embodiments of FIGS. 1, 2, and 3 can also be configured in this flowthrough configuration.

Various chemical reactions for activating the oxidant vapor to a higher oxidation state are contemplated. Looking to hydrogen peroxide, by way of example, hydroperoxy ions $HOO^-$ and singlet oxygen $^1O_2$ are potent oxidants. Analogous species and other potent oxidants can be delivered using gas phase delivery. In its simplest form, when the hydrogen peroxide makes contact with a surface, it transfers enough energy to the peroxide molecule for it to decompose into hydroxyl radicals. For example, $$H_2O_2 + M \rightarrow 2HO^-,$$

where M represents a collision with the biologically active substance, a wall, other object, other molecule, or the like. The hydroxyl radicals can go on to form other more reactive radicals by interactions with hydrogen peroxide and water vapor.

$$HO^- + H_2O_2 \rightarrow H_2O + HOO^-$$

$$HOO^- + HO^- \rightarrow {}^1O_2 + H_2O$$

Hydroxyl radicals $HO^-$, hydroperoxy radicals $HOO^-$, and singlet oxygen $^1O_2$ are all potent oxidants and are all present in hydrogen peroxide vapor to some degree. All of these radicals serve to inactivate biologically active substances including acetylcholineesterase inhibitors (VX, sarin, etc.), blistering agents (mustard gas, etc.), and biotoxins (botulinum toxin, etc.), biomolecules, pathogens, prions, and other similar biologically active molecules.

In addition to the radical generation steps, the hydrogen peroxide can dissolve or absorb onto/into the biologically active substance (i.e., dissolve into a liquid droplet, or absorb onto a solid particle). To enhance this dissolution/absorbtion, a cosolvent is added to the vapor and allowed to condense onto the surfaces of the equipment to be decontaminated. The solvent is selected as good solvents for the biologically active substances. By selecting a solvent, or solvents, miscible with water (and other polar solutes like hydrogen peroxide) but with lower polarity, the cosolvent layer can enhance the solubility of the hydrogen peroxide and its associated radical decomposition products in the biologically active substance so enhancing the rate of destruction. Examples of such cosolvent mixtures include: water and tert-butyl alcohol; water and acetonitrile; water, acetonitrile and isopropyl alcohol. By control of the mixture of solvent vapors, and hydrogen peroxide added to the enclosure, the composition of the condensate can be controlled to produce a liquid film on the surfaces to be decontaminated. By adding an alkaline gas soluble in the solvent mixture (ammonia for example), the pH of the condensed cosolvent layer can also be controlled. The presence of hydrogen peroxide in the condensate serves to lower the pH (35% aqueous $H_2O_2$ solution has a pH of approx. 3-4) and the ammonia can be added to raise the pH to the optimum value of around 8-9. Other suitable solvents include tetrahydrofuran, dimethylsulfoxide, acetone, acetaldehyde, propylene oxide, acetamide, diethylamine, and dimethoxyethane.

One way to enhance the generation of reactive radicals is by irradiating the enclosure with ultraviolet light at a wavelength that causes degradation of hydrogen peroxide. The increased degradation increases the concentration of radical intermediaries and enhances the decontamination effect.

Adding additional species to the hydrogen peroxide vapor also enhances the deactivation efficiency by increasing the number of reactive species present. Enhancing agents include ozone ($O_3$), alkenes ($CH_3CH=CHCH_3$ or more generally $RCH=CHR$), aldehydes (RCHO), and halogens ($Cl_2$, $Br_2$). For example, the addition of ozone increases the yield of radicals and the vapor stream.

$$O_3 + h \rightarrow O_2 + O^*$$

Where atomic oxygen $O^*$ is not a radical (all its electrons have paired spins), but is highly reactive.

$$O^* + H_2O \rightarrow 2HO^-$$

$$O^* + HOOH \rightarrow HO^- + HOO^-$$

As another example, short chain alkenes are also effective:

$$RCH=CHR + O_3 \rightarrow [\text{intermediates}] \rightarrow HO^- + HOO^-$$

This produces radicals from ozone with a higher yield.

Other molecules, such as aldehydes, result in the presence of alkyl peroxy radicals:

$$RCHO + HO^- \rightarrow RCO^- + H_2O$$

$$RCO^- + O_2 \rightarrow RC(O)OO^-$$

The product here is the alkyl peroxy radical, a radical of percarboxylic acid, i.e., if R is $CH_3$, this radical is formed from peracetic acid, another strong oxidant.

As another example, the addition of peroxycarboxylic acids (RC(O)OOH) to the reaction enhances the concentration of alkylperoxy radicals.

By controlling concentrations of small organic molecules, such as alkenes, alkanes, aldehydes, carboxylic and peroxy carboxylic acids, water vapor, hydrogen peroxide, and ozone, a steady-state concentration of the reactive radicals can be maintained.

Halogens are also suitable strong oxidants. Where X is any halogen:

$$X_2 + h \rightarrow 2X^-$$

$$X^- + HOOH \rightarrow HX + HOO^-$$

$$X^- + tBuOH \rightarrow HX + tBuO^-$$

Where tBuOH—tert butyl alcohol is added as part of the cosolvent system.

$$X^- + H_2O \rightarrow HX + HO^-$$

$$X^- + RCH_3 \rightarrow HX + RCH_2^-$$

It can be seen that adding appropriate species to the vapor mixture, a wide variety of radical species can be produced.

Strong oxidants are effective to attack biomolecules including proteins, such as anthrax toxin, botulinum toxin, and plague toxin. Breaking down such toxins into smaller protein chain fragments renders the toxins harmless. Similarly, reactions in which the oxidizing radicals break bonds and replace chemical groups around the phosphorous atom, e.g., a substitution reaction as in acetylcholine esterase inhibitors render these molecules non or less toxic. Similarly, oxidation of the sulfoxide or lysis at one of the sulphide-alkyl bonds renders blistering agent molecules non or less toxic.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A method of deactivating biologically active substances including:
   preheating objects contaminated with a biologically active substance to about 70° C.; and
   concurrently:
      subjecting the biologically active substances to a strong oxidant in a vapor phase; and
      subjecting the biologically active substances to ammonia gas.

2. The method as set forth in claim 1 wherein the biologically active substances arc biological or chemical warfare agents including one or more of chemical agents, pathogens, prions, and biotoxins.

3. The method as set forth in claim 2 wherein the chemical agents include nerve gas and blistering gas.

4. The method as set forth in claim 1 wherein the oxidant includes at least one of peroxy compounds, hypochlorites, halogen oxides, and ozone.

5. The method as set forth in claim 4 wherein the peroxy compounds include hydrogen peroxide.

6. The method as set forth in claim 1 further including:
   boosting the oxidation potential of the oxidant vapor rendering the vapor more reactive with the biologically active substances.

7. The method as set forth in claim 6 wherein boosting the oxidation potential includes at least one of:
   degrading the oxidant vapor with ultraviolet light; and,
   adding an enhancing agent.

8. The method as set forth in claim 1 further including:
   condensing a solvent vapor, mist, or fog on the biologically active substances.

9. The method as set forth in claim 8 wherein the solvent includes at least one of:
   tert-butyl alcohol,
   acetonitrile,
   isopropyl alcohol,
   tetrahydrofuran,
   dimethylsulfoxide,
   acetone, acetaldehyde,
propylene oxide,
acetamide,
diethylamine, and
dimethoxyethane.

10. The method as set forth in claim 8 further including:
subjecting the biologically active substances to an alkaline gas.

11. The method as set forth in claim 1 further including:
subjecting the biologically active substance to a chemical which at least one of:
raises the oxidation potential of the oxidant vapor rendering the oxidant vapor more reactive against the biologically active substance;
preconditions the biologically active substance;
reacts with the oxidant vapor to generate an intermediate compound that deactivates at least some of the biologically active substances;
increases a number and variety of free radical species in the oxidant vapors; and
adjusts pH.

12. A method o1 deactivating biologically active substances comprising:
preheating objects contaminated with a biologically active substances to about 70° C.;
subjecting the biologically active substances to a strong oxidant in a vapor phase; and
adding to the oxidant vapor at least one of:
ozone,
an alkene,
an aldehyde,
a peroxycarboxylic acid,
an alkane, and
carboxylic acid.

13. The method as set forth in claim 12 further including:
subjecting the biologically active substances to ammonia in a vapor phase concurrently with the vapor phase oxidant.

14. The method as set forth in claim 12 wherein the biologically active substances are biological or chemical warfare agents including one or more of chemical agents, pathogens, prions, and biotoxins.

15. The method as set forth in claim 14 wherein the chemical agents include at least one of nerve gas and blistering gas.

16. The method as set forth in claim 12 wherein the oxidant includes at least one of peroxy compounds, hypochlorates, and ozone.

17. The method as set forth in claim 16 wherein the peroxy compounds include hydrogen peroxide.

18. The method as set forth in claim 12 further including:
adding in vapor, mist, or fog form a second chemical that does at least one of:
raises the oxidation potential of the oxidant vapor rendering the oxidant vapor more reactive against the biologically active substance;
preconditions the biologically active substance;
reacts with the oxidant vapor to generate an intermediate compound that deactivates at least some of the biologically active substances;
increases a number and variety of free radical species in the oxidant vapors; and,
adjusts pH.

19. A method of deactivating biologically active substances on objects comprising:
preheating objects contaminated with the biologically active substance to about 70° C.;
subjecting the preheated biologically active substances to a strong oxidant in a vapor phase, the preheating allowing extraction of the biologically active substances from the object to facilitate reaction between the biologically active substances and the vapor phase oxidant when it is introduced.

20. The method as set forth in claim 19 further including:
subjecting the biologically active substances to an alkaline gas.

21. The method as set forth in claim 20 wherein the alkaline gas is used to raise a pH of the vapor phase oxidant to 8-9.

22. The method as set forth in claim 20 wherein the alkaline gas includes ammonia.

23. The method as set forth in claim 19 further including:
concurrently subjecting the biologically active substances to a chemical vapor, mist, or fog which at least one of:
raises the oxidation potential of the oxidant vapor rendering the oxidant vapor more reactive against the biologically active substance;
preconditions the biologically active substance;
reacts with the oxidant vapor to generate an intermediate compound that deactivates at least some of the biologically active substances;
increases a number and variety of free radical species in the oxidant vapors; and,
adjusts pH.

24. The method as set forth in claim 19 further including:
supplying ammonia vapor; mixing the ammonia vapor and the strong oxidant vapor; and
wherein in the subjecting step, the biologically active substances are subject to both the ammonia and strong oxidant vapors.

25. A method of deactivating biologically active substances comprising:
preheating objects contaminated with a biologically active substance to about 70° C.;
vaporizing a strong oxidant;
mixing the vaporized strong oxidant with an alkaline gas;
subjecting the biologically active substances to the mixture of the vaporized strong oxidant and alkaline gas.

26. The method as set forth in claim 25 wherein the alkaline gas includes ammonia in a gas phase.

27. The method as set forth in claim 26 wherein the strong oxidant is thermally vaporized.

28. A method of deactivating a chemical warfare agent comprising:
preheating the chemical warfare agent to about 70° C.
vaporizing hydrogen peroxide;
mixing the vaporized hydrogen peroxide with vapor phase ammonia; and
subjecting the chemical warfare agent to the mixture of the vaporized hydrogen peroxide and ammonia at a temperature of 45-60° C.

29. The method as set forth in claim 28, further including:
heating objects contaminated by the biologically active substance to about 70° C.

* * * * *